United States Patent [19]

Scherrer et al.

[11] Patent Number: 5,049,572

[45] Date of Patent: Sep. 17, 1991

[54] SUBSTITUTED DI-T-BUTYLPHENOLS AND ANTI-ALLERGIC USE THEREOF

[75] Inventors: Robert A. Scherrer, White Bear Lake; Mark A. Rustad, Afton, both of Minn.

[73] Assignee: Riker Laboratories, Inc., St. Paul, Minn.

[21] Appl. No.: 593,342

[22] Filed: Oct. 1, 1990

Related U.S. Application Data

[63] Continuation of Ser. No. 168,864, Mar. 16, 1988, abandoned, which is a continuation-in-part of Ser. No. 34,537, Apr. 6, 1987, abandoned.

[51] Int. Cl.$^5$ .................. C07C 103/85; C07D 257/04; A61K 31/41; A61K 31/165
[52] U.S. Cl. ..................... 514/381; 514/563; 548/253; 548/252; 548/251; 562/452; 562/453; 562/455; 562/457
[58] Field of Search ............... 548/253; 562/452, 455; 514/381, 563

[56] References Cited

U.S. PATENT DOCUMENTS

| | | | |
|---|---|---|---|
| 4,070,484 | 1/1978 | Harita et al. | 424/319 |
| 4,094,857 | 6/1978 | Wolfe, Jr. | 260/45.9 |
| 4,153,728 | 5/1979 | Wolff et al. | 424/319 |
| 4,322,439 | 3/1982 | Klemm et al. | 424/319 |
| 4,710,515 | 12/1987 | Kirk et al. | 514/563 |
| 4,714,776 | 12/1987 | Bell et al. | 562/460 |
| 4,716,178 | 12/1987 | Scherrer | 514/563 |

FOREIGN PATENT DOCUMENTS 181568  5/1986  European Pat. Off. .

OTHER PUBLICATIONS

Chemical Abstracts, 69, 58954e (1968).
Chemical Abstracts, 72, 68160u (1970).

Primary Examiner—David B. Springer
Attorney, Agent, or Firm—Gary L. Griswold; Walter N. Kirn; Robert W. Sprague

[57] ABSTRACT

Novel compounds which are 2,6-di-t-butylphenols substituted in the 4 position by a carbamyl or acylamino group, which carbamyl or acylamino group is substituted by a group which includes an acidic substituent are useful as inhibitors of leukotriene biosynthesis and as antiallergic agents. Pharmacological methods for using such compounds and synthetic intermediates for preparing such compounds are also disclosed.

26 Claims, No Drawings

SUBSTITUTED DI-T-BUTYLPHENOLS AND ANTI-ALLERGIC USE THEREOF

CROSS-REFERENCE TO RELATED APPLICATION

This application is a continuation of Ser. No. 168, 864, Mar. 16, 1988, abandoned, which is continuation-in-part of copending application Ser. No. 034,537, filed, Apr. 6, 1987, abandoned.

TECHNICAL FIELD

This invention relates to substituted di-t-butylphenols which are inhibitors of leukotriene synthesis. This invention further relates to pharmaceutical compositions containing such compounds, pharmacological methods for using such compounds and synthetic intermediates for preparing such compounds.

BACKGROUND OF THE INVENTION

The leukotrienes are a group of biologically active mediators derived from arachidonic acid through the action of lipoxygenase enzyme systems. The leukotrienes are potent smooth muscle contracting agents, particularly on respiratory smooth muscle, but also on other tissues as well. In addition, they promote mucous production, modulate vascular permeability changes and are potent inflammatory mediators in human skin. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis ("SRS-A").

The most important compound in the second group of leukotrienes, namely dihydroxy fatty acids, is Leukotriene $B_4$. This compound is a potent chemotactic agent for neutrophils and eosinophils and, in addition, may modulate a number of other functions of these cells. It also affects other cell types such as lymphocytes and, for example, may modulate the action of suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a lipoxygenase enzyme. See, for example, D M. Bailey et al., Ann. Rpts. Med. Chem., 17, 203 (1982).

RESPIRATORY CONDITIONS

Asthma. The leukotrienes are potent spasmogens of human trachea, bronchus, and lung parenchymal strip, and when administered to normal volunteers as aerosols are 3,800 times more potent than histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. Lipoxygenase products are also thought to be regulators of mast cell degranulation, and recent studies with human lung mast cells have suggested that lipoxygenase inhibitors (but not corticosteroids), may suppress antigen-induced mast cell degranulation. In vitro studies have shown that antigen challenge of human lung results in the release of leukotrienes and that, in addition, purified human mast cells can produce substantial amounts of leukotrienes. There is, therefore, good evidence that the leukotrienes are important mediators of human asthma. Lipoxygenase inhibitors would therefore be a new class of drugs for the treatment of asthma. See, for example, B. Samuelsson, Science, 220, 568–575 (1983).

SKIN DISEASES

Psoriasis. Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in non-involved skin, in biologically significant amounts.

ALLERGIC CONDITIONS

Leukotrienes can be measured in nasal washings from patients with allergic rhinitis and are greatly elevated following antigen challenge. Leukotrienes may mediate this disease through their ability to regulate mast cell degranulation, to modulate mucous production and mucocillary clearance, and to mediate the accumulation of inflammatory leukocytes.

Leukotrienes may also mediate other diseases. These include atopic dermatitis, gouty arthritis, gall bladder spasms and ulcerative colitis. In addition, they may have a role in cardiovascular disease because Leukotrienes $C_4$ and $D_4$ act as coronary and cerebral arterial vasoconstrictors and these compounds may also have negative inotropic effects on the myocardium. In addition, the leukotrienes are important mediators of inflammatory disease through their ability to modulate leukocyte and lymphocyte function.

Many substituted di-t-butylphenols are known. Generally these compounds may be useful as antioxidants. Some of these compounds are also known to be active antiinflammatory agents.

DETAILED DESCRIPTION OF THE INVENTION

The present invention relates to compounds of Formula I:

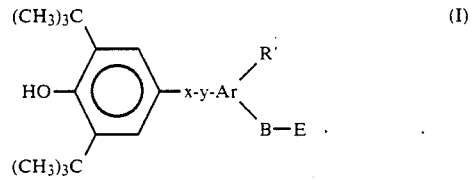

wherein x is carbonyl or N-R, and y is carbonyl or N-R; with the proviso that when x is carbonyl, y is N-R, and when x is N-R, y is carbonyl; further provided that:

· 1)
  when x is N-R,
    R is hydrogen,
    R' is hydrogen,

B is a carbon-carbon bond,
Ar is phenyl or cyclohexyl, and
E is tetrazolyl or carboxyl,
with the proviso that when Ar is cyclohexyl, E is carboxyl and is alpha to the carbonyl-cyclohexyl bond; and 2)
when x is carbonyl,
R is hydrogen or lower alkyl,
R' is hydrogen, halogen, trifluoromethyl, lower alkyl or lower alkoxy,
Ar is phenyl, E is carboxyl, tetrazolyl, or N-methyltetrazolyl, and
B is as follows:
when E is carboxyl, B is a carbon-carbon bond; an alkylene group containing one to about seven carbon atoms; or an alkylene group containing one to about seven carbon atoms and being either (a) interrupted by an ether linkage, a thioether linkage or a carbon-carbon double bond, or (b) attached to the phenyl ring by an oxygen atom or an unoxidized sulfur atom; or
when E is tetrazolyl or N-methyltetrazolyl, B is a carbon-carbon bond; an alkylene group containing one to about four carbon atoms; an alkylene group containing one to about four carbon atoms and being either (a) interrupted by an ether linkage, a thioether linkage or a carbon-carbon double bond, or (b) attached to the phenyl ring by an oxygen atom or an unoxidized sulfur atom; an unoxidized sulfur atom or carboxamido;
and a derivative of the compound wherein E is carboxyl, selected from the group consisting of lower alkyl esters, (lower)alkylamino(lower)alkyl esters, esters of glycolamide, pharmaceutically acceptable (lower)alkylamino(lower)alkyl ester acid-addition salts and pharmaceutically acceptable carboxylate salts;
and a derivative of the compound wherein E is tetrazolyl, selected from pharmaceutically acceptable alkali metal and alkaline earth salts of the tetrazolyl moiety.

Compounds of Formula I are useful to inhibit bronchoconstriction due to allergic response and to inhibit leukotriene synthesis The present invention also provides novel compounds of Formula II below

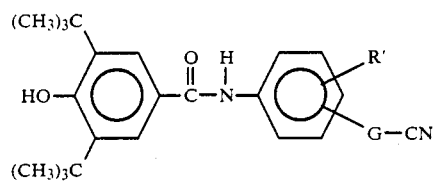

wherein
R' is hydrogen, halogen, trifluoromethyl, lower alkyl or lower alkoxy; and
G is a carbon-carbon bond or alkylene of one to about four carbon atoms.

Furthermore, the present invention also provides novel compounds of Formula III below

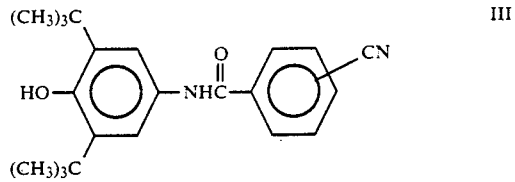

Compounds of Formula II and III are useful synthetic intermediates for preparing certain of the compounds of Formula I.

The preferred compounds of Formula I of the invention are those wherein B is a carbon-carbon bond.

Another preferred subset of compounds of Formula I are those wherein X is carbonyl.

When R is lower alkyl it is presently preferred to be methyl. The presently preferred R group is hydrogen.

By "lower" as used in connection with "alkyl" is meant that such groups contain one to about four carbon atoms. Most preferred alkyl groups contain one to about two carbon atoms. By "lower" as used in connection with "alkylene" is meant that such groups contain two to about four carbon atoms.

In the compounds of Formula I wherein E is tetrazolyl, two tautomeric forms of tetrazolyl exist as is known to those skilled in the art. Tautomerism does not exist in tetrazolyl moieties where the tetrazolyl ring is substituted on a nitrogen atom by methyl. Instead, two N-methyl isomers are obtained, one in which the methyl group is in the 1-position, the other in which it is in the 2-position. All such tautomers and isomers are within the scope of this invention.

It is well known to the art that pharmaceutically acceptable salts such as alkali metal, alkaline earth, aluminum and other metal and amine salts of pharmaceutically active acids are the equivalents of the acids in terms of activity, and in some cases may even offer advantages in absorption, formulation and the like. Pharmaceutically-acceptable carboxylate salts of the compounds of the invention which contain carboxyl as E are prepared in an inert atmosphere by reaction of the acid with a base and subsequent evaporation to dryness, preferably under mild conditions. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in a selected solvent.

Other useful derivatives of the compounds of the invention which contain carboxyl as E include alkyl esters, alkylaminoalkyl esters, and salts of the latter. In the ester derivatives, the hydrogen portion of the carboxylic acid group is replaced with an alkyl or substituted alkyl, preferably an alkylaminoalkyl group.

Esters of the compounds of the invention may be obtained as intermediates during the preparation of the corresponding acid. In some cases, the esters may be prepared directly using standard synthetic methods. These esters may exhibit antiallergic activity, but they are primarily of interest as synthetic intermediates, although in some instances hydrolyzable or salt-forming esters may be of interest as therapeutic agents.

Ester derivatives may be obtained by alkylation of an alkali metal salt of the compound in dimethylformamide with an alkyl iodide or dialkylaminoalkylchloride, or by starting with esters instead of acids in Reaction Scheme A below.

Pharmaceutically acceptable alkali metal and alkaline earth salts may also be prepared of compounds of Formula I wherein E is tetrazolyl by methods known to those skilled in the art.

Compounds of Formula I wherein x is carbonyl, y is N-R, and E is —COOH (with R, R', Ar and B being as defined previously in the context of Formula I) may be prepared in accordance with the procedures of Reaction Scheme A below.

REACTION SCHEME A

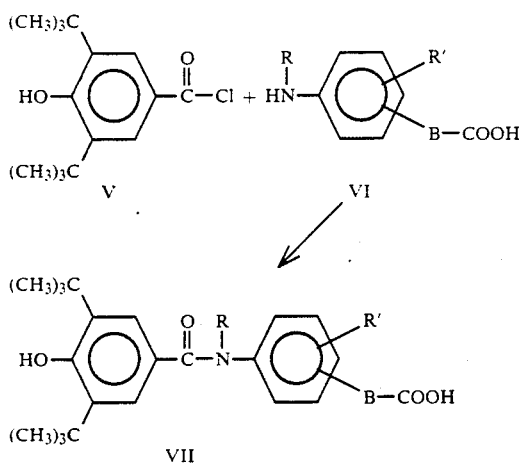

In Reaction Scheme A, known 3,5-di-t-butyl-4-hydroxybenzoyl chloride (V) is reacted with an amine of Formula VI to provide a compound of Formula VII which is a subgenus of Formula I. The reaction is conducted by combining the 3,5-di-t-butyl-4-hydroxybenzoyl chloride with 2 to 2.5 equivalents of an amine of Formula VI in an inert solvent such as 1,2-dimethoxyethane, accompanied by gentle heating if necessary. Amines of Formula VI are known compounds or may be prepared using known methods. Examples of amines of Formula VI are m-aminobenzoic acid, p-aminobenzoic acid, o-aminobenzoic acid (anthranilic acid), p-aminophenyl acetic acid and the like.

The product of Formula VII may be readily isolated and purified, for example, by recrystallization.

Compounds of Formula I wherein x is carbonyl, y is N-R, and E is tetrazolyl (with R, R', Ar and B being as defined previously in the context of Formula I) may be prepared in accordance with the procedures of Reaction Scheme B below.

REACTION SCHEME B

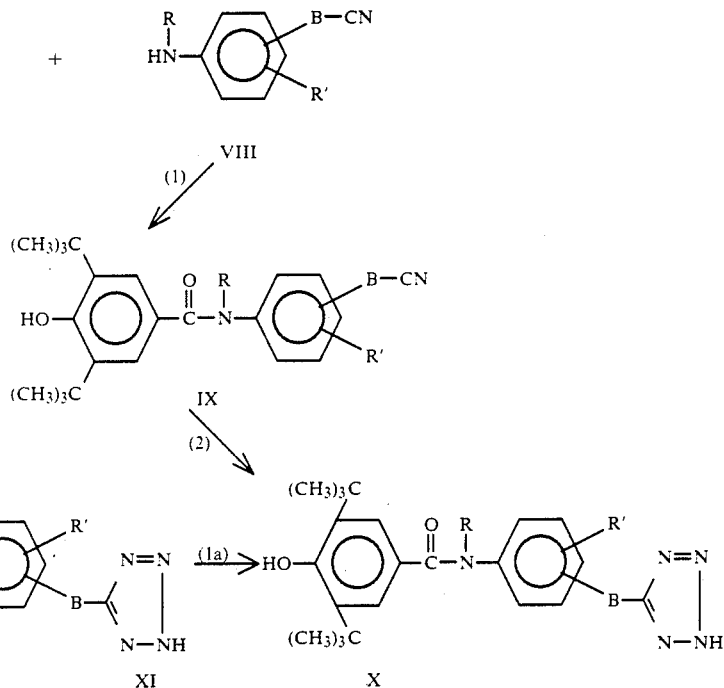

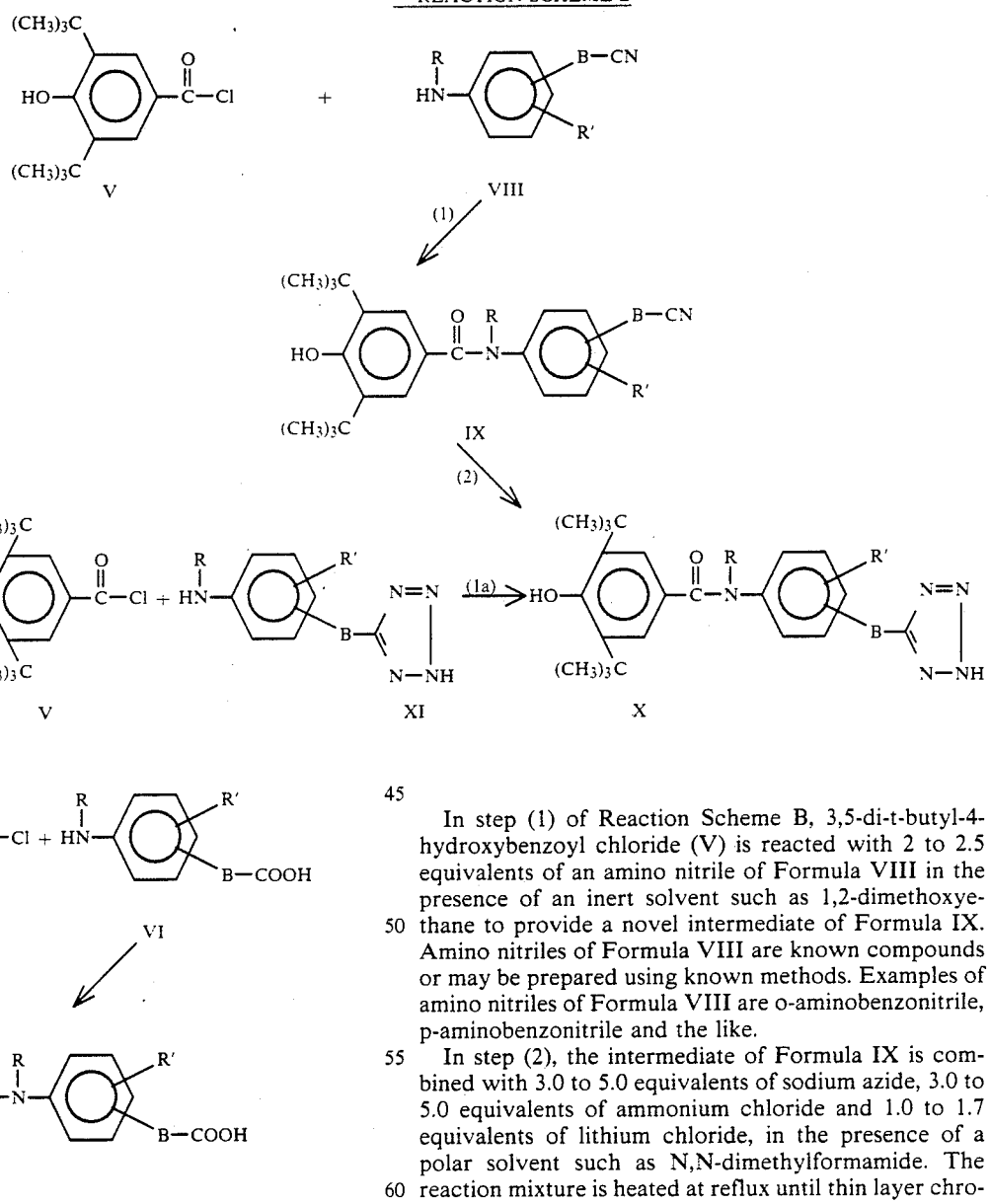

In step (1) of Reaction Scheme B, 3,5-di-t-butyl-4-hydroxybenzoyl chloride (V) is reacted with 2 to 2.5 equivalents of an amino nitrile of Formula VIII in the presence of an inert solvent such as 1,2-dimethoxyethane to provide a novel intermediate of Formula IX. Amino nitriles of Formula VIII are known compounds or may be prepared using known methods. Examples of amino nitriles of Formula VIII are o-aminobenzonitrile, p-aminobenzonitrile and the like.

In step (2), the intermediate of Formula IX is combined with 3.0 to 5.0 equivalents of sodium azide, 3.0 to 5.0 equivalents of ammonium chloride and 1.0 to 1.7 equivalents of lithium chloride, in the presence of a polar solvent such as N,N-dimethylformamide. The reaction mixture is heated at reflux until thin layer chromatography indicates that the reaction is complete. The product of Formula X, which is a subgenus of Formula I, is readily isolated and may be purified, for example, by recrystallization from a polar solvent.

Hydrolysis of the intermediate of Formula IX using conventional methods may also be undertaken to provide the corresponding compounds of Formula I wherein E is —COOH. Conditions are chosen to afford a preferential hydrolysis of the CN group over the —CONH— functionality using mild conditions known to those skilled in the art.

In alternative step (1a) of Reaction Scheme B, 3,5-di-t-butyl-4-hydroxybenzoyl chloride (V) is combined with 2 to 2.5 equivalents of an amine of Formula XI in the presence of an inert solvent such as 1,2-dimethoxyethane. The product of Formula X again may be readily isolated and purified. Amines of Formula XI are known compounds or may be prepared using conventional methods. Examples of amines of Formula XI are 3-(1H-tetrazol-5-yl)benzeneamine, 4-(1H-tetrazol-5-yl)benzeneamine, and the like.

Compounds of Formula I wherein x is carbonyl, y is N-R, Ar is phenyl and E is N-methyltetrazolyl (with R, R', and B being as defined previously) may be prepared by alkylating an alkali metal salt of the corresponding compound of Formula I, wherein E is tetrazolyl, with methyl iodide.

Compounds of Formula I wherein Ar is phenyl, x is N-H, y is carbonyl, and E is carboxyl (with R, R' and B being as defined previously in the context of Formula I) may be prepared in accordance with the procedure of Reaction Scheme C below.

REACTION SCHEME C

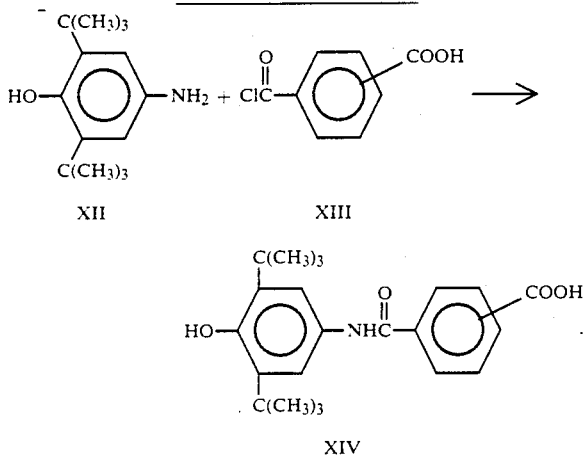

In Reaction Scheme C, known 4-amino-2,6-di-t-butylphenol (XII) is reacted with an acid chloride of formula XIII to provide a compound of Formula XIV which is a subgenus of Formula I. The reaction is conducted by combining the 4-amino-2,6-di-t-butylphenol with an acid chloride of Formula XIII in an inert solvent such as methylene chloride in the presence of triethylamine. Examples of acid chlorides of Formula XIII are m-(chloroformyl)benzoic acid and p-(chloroformyl)benzoic acid. Alternatively, a derivative of the acyl chloride of Formula XIII, wherein the carboxylic acid is esterified, may be reacted with 4-amino-2,6-di-t-butylphenol (XII). Hydrolysis of the product provides a compound of Formula XIV. The product of Formula XIV may be readily isolated and purified using standard techniques.

Compounds of Formula I wherein x is N-R, y is carbonyl, E is carboxyl (with R, R', B and Ar being as defined previously in the context of Formula I) and the carbonyl and carboxyl bonds are alpha to one another may be prepared in accordance with the procedure of Reaction Scheme D below.

REACTION SCHEME D

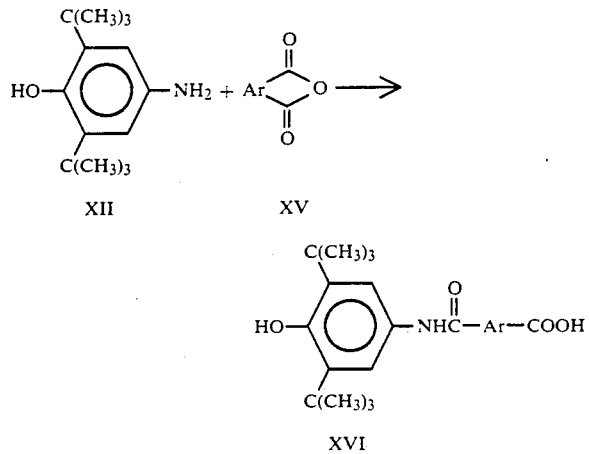

In reaction Scheme D, known 4-amino-2,6-di-t-butylphenol (XII) is reacted with an anhydride of Formula XV to provide a compound of Formula XVI which is a subgenus of Formula I. The reaction is conducted by combining the 4-amino-2,6-di-t-butylphenol with one equivalent of an anhydride of Formula XV in a solvent such as diethyl ether or 1,2-dimethoxyethane. Examples of anhydrides of Formula XV are phthalic anhydride, cis-1,2-cyclohexanedicarboxylic anhydride and trans-1,2-cyclohexanedicarboxylic anhydride. The product of Formula XVI may be readily isolated and purified, for example, by recrystallization.

Compounds of Formula I wherein x is N-R, y is carbonyl, Ar is phenyl and E is tetrazolyl (with R, R' and B being as defined previously in the context of Formula I) may be prepared in accordance with the procedures of Reaction Scheme E below.

REACTION SCHEME E

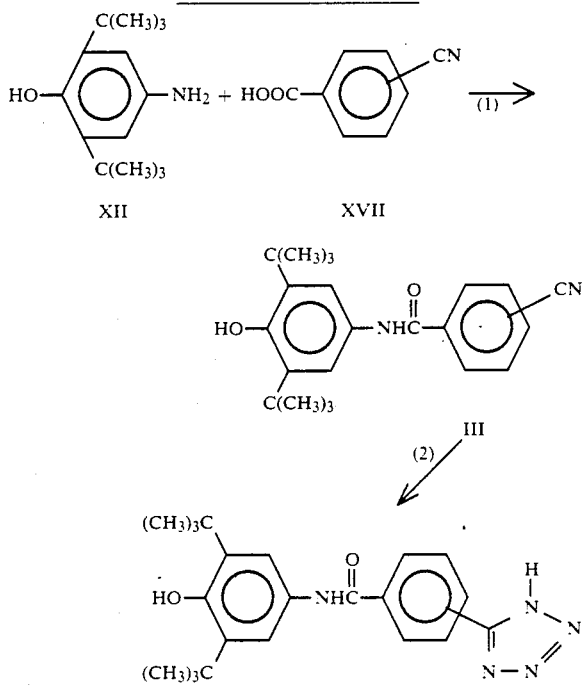

In step (1) of Reaction Scheme E, 4-amino-2,6-di-t-butylphenol (XII) is reacted with one equivalent of a cyanobenzoic acid of Formula XVII in the presence of dicyclohexylcarbodiimide in a solvent such as tetrahydrofuran to provide a novel intermediate of Formula III. Examples of cyanobenzoic acids of Formula XVII are 3-cyanobenzoic acid and 4-cyanobenzoic acid. Alternatively, compounds of Formula III may be prepared using cyanobenzoyl chlorides in a process analogous to that shown in Reaction Scheme C.

In step (2), the intermediate of Formula III is combined with three equivalents of sodium azide, three equivalents of ammonium chloride and one equivalent of lithium chloride in the presence of a polar solvent such as N,N-dimethylformamide. The reaction mixture is heated at about 90° C. until thin layer chromatography indicates that the reaction is complete. The product of Formula XVIII, which is a subgenus of Formula I, is readily isolated and may be purified, for example, by recrystallization.

The activity of the compounds of Formula I may be demonstrated readily by in vivo testing. The in vivo test used to demonstrate antiallergic activity of the compounds of Formula I may be any of those known to those skilled in the art. Preferably, bronchoconstriction in sensitized guinea pigs is measured upon antigen challenge. This test is described in broad terms by Piechuta et al., *Immunology*, 38, 385 (1979), incorporated herein by reference, and more specifically by Hammerbeck and Swingle, *Int. Archs. Allergy Appl. Immun.* 74, 84-90 (1984), incorporated herein by reference. It is used in a modified form as follows: Male Hartley guinea pigs (250-600g) are pretreated with an antihistamine, for example, chlorpheniramine, and then dosed intraperitoneally with a compound of the invention at a level of about 1 to 40 mg/kg 15 minutes prior to challenge. The animals are placed under an inverted dessicator jar ($18 \times 14$ cm) with a constant flow of air coming into the chamber from a compressed-air source to prevent hypoxia, and are aerosol-challenged with either water, or with ovalbumin at a concentration of 10 mg per ml. Air flow leaving the chamber and fluctuations due to respiration are monitored through a separate outlet with a Fleisch No. 0000 pneumotachograph (available from Beckman Instruments, Inc. Schiller Park, IL.) coupled to a Beckman Type R dynograph (available from Beckman Instruments, Inc.). Aerosolization through a third outlet is made via a No. 4 DeVilbiss nebulizer (available from The DeVilbiss Company, Somerset, PA) for 90 seconds at 150 mm Hg. The characteristic respiratory patterns observed are summations of two air exchange processes occurring simultaneously in the chamber. One exchange process is due to inspiration and expiration of air into and out of the animal, while the other exchange process is due to the air flow into and out of the chamber due to respiratory movements. The tracing obtained is the mechanical representation of the summation of those flows. Superimposed on the tracings is a characteristic spiking ("notching"), which appears to be an exaggerated expiratory movement, the frequency of which correlates with the severity of the bronchoconstrictive reaction. The frequency of notching for 15-minute periods beginning 4 minutes after the beginning of the aerosol challenge is used for comparing various treatments. Effects are considered significant if the t value achieves $p<0.05$. The tested compounds of Formula I exhibit an intraperitoneal $ED_{40}$ of 100 mg per kg or less when tested in the above model. Preferred compounds exhibit an $ED_{40}$ of 50 mg per kg or less and most preferred compounds are active at 25 mg per kg or less.

The oral activity of compounds of Formula I may be demonsrated using the Konzett-Rossler in vivo test method. The activity is determined according to the procedure which follows. The Konzett-Rossler technique (H.Konzett and R. Rossler, Naunyn-Schmiedbergs Arch. Pharmakol., 195, 71-74, 1940, incorporated herein by reference) is used to assess the effect of compounds of Formula I of the invention on antigen challenge of male Hartley strain guinea pigs (350-500g). Fourteen days after sensitization with ovalbumin (50 mg/kg intraperitoneally) guinea pigs are anesthetized with pentobarbital (70 mg/kg intraperitoneally) and spontaneous respiration is eliminated with succinylcholine (2 mg/kg intraperitoneally). The trachea is cannulated and respiration is maintained under positive pressure with a minature ventilator (5 ml/breath, 87 breaths/minute, 10 cm water). Bronchoconstrictor responses are represented as increased excursions of the tracing on a physiological recorder of air overflow to the lungs measured by a pneumotachograph in series with a differential pressure transducer. The guinea pigs are pretreated with an antihistamine, for example, chlorpheniramine, and are then dosed orally at a level of about 5 to 40 mg/kg with a suspension of a compound of Formula I of the invention in 4% aqueous acacia. The animals are challenged with ovalbumin (300 $\mu$g/kg intravenously) thirty (30) minutes later.

The compound of Example 7 demonstrated good oral activity in the test method described above.

The compounds may also be tested in more specific tests for the inhibition of leukotriene synthesis. Active compounds are those which exhibit an $IC_{50}$ of 100 micromolar or less, and preferably less than 25 micromolar. Most preferred compounds exhibit an $IC_{50}$ of 10 micromolar or less. The compounds are tested in either intact cells or in cell sonicate. The intact cell assay is similar to that described by Verhagen et al., FEBS Letter 168, 23-28 (1984), incorporated herein by reference. Human leukocytes are prepared using standard procedures. The cells are incubated in pH 7.4 Tris buffer containing 5 millimolar calcium chloride and 5 millimolar glutathione. After vehicle or drug incubation, the cells are activated with the calcium ionophore A 23187 (4 micrograms per ml.) After 15 minutes at room temperature, the cells are centrifuged and the supernatants are stored for assay of $LTC_4$ content by radioimmunoassay. The cell sonicate assay utilizes the cell free leukotriene biosynthesis system of M. Steinhoff et al., Biochim. Biophy. Acta., 68, 28 (1980), incorporated herein by reference, which consists of homogenized rat basophil leukemia cells. Leukotriene synthesis is initiated by the addition of arachidonate. Solutions are centrifuged and supernatants assayed using a radioimmunoassay developed as described by Aeringhaus et al., FEBS Letter 146, 111-114, incorporated herein by reference. Drugs are dissolved in ethanol or dimethyl sulfoxide and preincubated for five minutes. Phenidone is used as a positive control.

Thus, compounds of Formula I are antiallergic agents exhibiting in vivo activity in mammals. The pharmaceutical compositions of the present invention will contain sufficient compound of Formula I in a dosage form suitable for inhibiting the mammalian biosynthesis of leukotrienes, or for the treatment desired. The effective concentration of the Formula I compound in the composition will vary as required by the mode of administration, dosage form, and pharmacological effect and level desired.

For treating pulmonary conditions such as asthma, the mode of administration may be oral, parenteral, by inhalation, by suppository and the like. Suitable oral dosage forms are tablets, elixirs, emulsions, solutions or capsules, including delayed or sustained release dosage forms. Dosage forms for administration by inhalation include aerosols and sprays and will be administered in metered doses if desired.

For treating other allergies or allergic reactions, the compound of Formula I may be administered by any conventional mode, for example, orally, parenterally, topically, subcutaneously, by inhalation and the like. The oral and parenteral dosage forms are as described for pulmonary treatment. The topical application dosage forms include ointments, sprays, controlled release patches, powders, solutions and the like.

For treating inflammation, the mode of administration may be oral, parenteral, by suppository and the like. The various dosage forms are as described above.

For treating skin diseases such as psoriasis, atopic dermatitis and the like, oral, topical or parenteral administration is useful. For topical application to the diseased area salves, patches, controlled release patches, emulsions, etc. are convenient dosage forms.

For treating cardiovascular conditions any suitable mode of administration such as oral or parenteral may be used.

In addition to the common dosage forms listed above, the compounds of Formula I may also be administered for various utilities and indications or for inhibiting leukotriene synthesis by conventional controlled release means and/or delivery devices.

In preparing suitable dosage forms, conventional compounding procedures and ingredients, for example, diluents, carriers, etc. may be used. Examples of suitable solid carriers are lactose, terra alba, sucrose, talc, gelatin, agar, pectin, acacia, magnesium stearate, stearic acid, and the like. Examples of suitable liquid carriers are syrup, peanut oil, olive oil, water, a polyethylene glycol such as "PEG 400" (available from Union Carbide) and the like. Similarly, the carrier or diluent can include any time delay material well known to the art, such as glyceryl monostearate or glyceryl distearate, these being useful alone or, for example, in combination with wax.

The following examples are provided to illustrate the invention, but are not intended to be limiting thereof.

EXAMPLE 1

Preparation of
N-(3-Carboxyphenyl)-3,5-Di-t-Butyl-4-Hydroxybenzamide

A solution of 8.6g (0.063 mole) of m-aminobenzoic acid in 200 ml of 1,2-dimethoxyethane was mixed with a suspension of 8.0g (0.0298 mole) of 3,5-di-t-butyl-4-hydroxybenzoyl chloride in 100 ml of 1,2-dimethoxyethane, and the mixture was stirred at 25° C. for one hour. The reaction mixture was then filtered. The filtrate was thereafter diluted with 300 ml of water and cooled to give the crude product as a white solid. This material was recrystallized from a mixture of ethanol and water to give 5.6g of white solid N-(3-carboxyphenyl)-3,5-di-t-butyl-4-hydroxybenzamide, m.p. 279°-280° C. Analysis: Calculated for $C_{22}H_{27}NO_4$: %C, 71.5; %H, 7.4; %N, 3.8; Found: %C, 72.0; %H, 7.3; %N, 3.7.

EXAMPLE 2

Preparation of
N-(4-Carboxyphenyl)-3,5-Di-t-Butyl-4-Hydroxybenzamide

A solution of 8.6g (0.063 mole) of p-aminobenzoic acid in 100 ml of 1,2-dimethoxyethane was added to a suspension of 8.0g (0.0298 mole) of 3,5-di-t-butyl-4-hydroxybenzoyl chloride in 100 ml of 1,2-dimethoxyethane, and the mixture was stirred at room temperature for 16 hours. The reaction mixture was then filtered. The filtrate was thereafter diluted with 200 ml of water and chilled. The resulting precipitate was collected, and was then recrystallized from a mixture of ethanol and water to give 3.6g of white needles of N-(4-carboxyphenyl)-3,5-di-t-butyl-4-hydroxybenzamide, m.p. 265°-266° C. Analysis: Calculated for $C_{22}H_{27}NO_4$: %C, 71.5; %H, 7.4; %N, 3.8; Found: %C, 71.7; %H, 7.3; %N, 3.6.

EXAMPLE 3

Preparation of
N-(2-Carboxyphenyl)-3,5-Di-t-Butyl-4-Hydroxybenzamide

A solution of 8.6g (0.063 mole) of anthranilic acid in 50 ml of 1,2-dimethoxyethane was added to a suspension of 8.0g (0.0298 mole) of 3,5-di-t-butyl-4-hydroxybenzoyl chloride in 150 ml of 1,2-dimethoxyethane. The reaction mixture was heated at approximately 75° C. for 30 minutes after which time it was stirred for 48 hours at room temperature. The reaction mixture was then filtered, and the filtrate was evaporated to give the crude product as an oil. This oil was triturated with a mixture of ethanol and water to give a solid which was recrystallized twice from a mixture of ethanol and water to give 5.3g of white crystalline N-(2-carboxyphenyl)-3,5-di-t-butyl-4-hydroxybenzamide, m.p. 202°-203° C. Analysis: Calculated for $C_{22}H_{27}NO_4$: %C, 71.5; %H, 7.4; %N, 3.8; Found: %C, 71.4; %H, 7.5; %N, 3.7.

EXAMPLE 4

Preparation of
4-(3,5-Di-t-Butyl-4-Hydroxybenzamido)phenylacetic Acid

A suspension of 9.2g (0.061 mole) of p-aminophenylacetic acid in 150 ml of 1,2-dimethoxyethane was added to a suspension of 8.0g (0.0298 mole) of 3,5-di-t-butyl-4-hydroxybenzoyl chloride in 100 ml of 1,2-dimethoxyethane, and the resulting mixture was stirred at room temperature for 12 hours. The reaction mixture was then filtered. The filtrate was thereafter diluted with water and chilled. The resulting precipitate was collected and recrystallized from a mixture of ethanol and water to give 1.32g of yellow crystalline 4-(3,5-di-t-butyl-4-hydroxybenzamido)phenylacetic acid, m.p. 253°-254° C. Analysis: Calculated for $C_{23}H_{29}NO_4$: %C, 72.0; %H, 7.6; %N, 3.6; Found: %C, 72.0; %H, 7.7; %N, 3.4.

EXAMPLE 5

Preparation of N-(3-Carboxy-4-chlorophenyl)-3,5-di-t-butyl-4-hydroxybenzamide A suspension of 6.90 g (0.04 mole) of 5-amino-2-chlorobenzoic acid in 100 ml of 1,2-dimethoxyethane was mixed with a solution of 5.08g (0.02 mole) of 3,5-di-t-butyl-4-hydroxybenzoyl chloride in 100 ml of 1,2-dimethoxyethane, and the mixture was stirred at 25° C. for about 72 hours. The reaction mixture was heated gently for 30 minutes and then allowed to cool before being filtered to remove the hydrochloride salt of the excess starting amine. The filtrate was concentrated under vacuum and then diluted with water. The resulting precipitate was collected, and was then recrystallized twice from a mixture of ethanol and water to give 2.8g of off-white solid N-(3-carboxy-4-chlorophenyl)-3,5-di-t-butyl-4-hydroxybenzamide, m.p. 265°–267° C. Analysis: Calculated for $C_{22}H_{26}NO_4Cl$: %C, 65.4; %H, 6.5; %N, 3.4; Found: %C, 65.8; %H, 6.6; %N, 3.5.

EXAMPLE 6

Preparation of N-(5-Carboxy-2-methoxyphenyl)-3,5-di-t-butyl-4-hydroxybenzamide A solution of 5.06g (0.02 mole) of 3,5-di-t-butyl-4-hydroxybenzoyl chloride in 100 ml of 1,2-dimethoxyethane was mixed with a solution of 6.69g (0.04 mole) of 3-amino-4-methoxybenzoic acid in 125 ml of 1,2-dimethoxyethane, and the mixture was stirred at 25° C. for about 16 hours. The reaction mixture was heated gently for 30 minutes and then allowed to cool before being filtered to remove the hydrochloride salt of the excess starting amine. The filtrate was concentrated under vacuum and then diluted with water. The resulting precipitate was collected and was then recrystallized three times from a mixture of ethanol and water to give 1.9g of white solid N-(5-carboxy-2-methoxyphenyl)-3,5-di-t-butyl-4-hydroxybenzamide, m.p. 259°–261° C. Analysis: Calculated for $C_{23}H_{29}NO_5$: %C, 69.2; %H, 7.3; %N, 3.5; Found: %C, 69.3; %H, 7.3; %H, 3.6.

EXAMPLE 7

Preparation of 5-[3-(3,5-di-t-butyl-4-hydroxybenzamido)phenyl]tetrazole hydrate Part A Under a nitrogen atmosphere, a solution of 9.02 g (0.033 mole) of 3,5-di-t-butyl-4-hydroxybenzoyl chloride in 75 ml of 1,2-dimethoxyethane was mixed with a solution of 7.93g (0.067 mole) of 3-aminobenzonitrile in 75 ml of 1,2-dimethoxyethane. The resulting mixture was stirred at 25° C. for an hour and then heated to a gentle reflux for about five hours. The mixture was allowed to cool and the resulting precipitate was collected and dried to give 10.3g of a tan crystalline solid. This material was then recrystallized from ethanol. Two different crops were obtained. The first gave 4.6g of an off-white crystalline material, m.p. 267°–269° C. The second gave 2.4g of white crystalline N-(3-cyanophenyl)-3,5-di-t-butyl-4-hydroxybenzamide, m.p. 265°–267° C. Analysis: Calculated for $C_{22}H_{26}N_2O_2$: %C, 75.4; %H, 7.5; %N, 8.0; Found: %C, 75.4; %H, 7.5; %N, 7.8.

Part B

A solution of 5.16g (0.015 mole) of N-(3-cyanophenyl)-3,5-di-t-butyl-4-hydroxybenzamide, 2.95g (0.045 mole) of sodium azide, 2.48g (0.045 mole) of ammonium chloride and 0.65g (0.015 mole) of lithium chloride in 30 ml of N,N-dimethylformamide was heated under a nitrogen atmosphere in a stoppered flask at about 120° C. for about 60 hours. The reaction mixture was allowed to cool before being poured into a mixture of 10% hydrochloric acid and ice. The resulting precipitate was collected and then recrystallized from a mixture of ethanol and water to give 2.8g of off-white solid 5-[3-(3,5-di-t-butyl-4-hydroxybenzamido)phenyl]tetrazole hydrate, m.p. 184°–193° C. Analysis: Calculated for $C_{22}H_{27}N_5O_2.H_2O$: %C, 64.5; %H, 6.9; %N, 17.8; Found: %C, 64.9; %H, 7.0; %N, 17.4.

EXAMPLE 8

Preparation of 2-[N-(3,5-Di-t-butyl-4-hydroxyphenyl)carbamoyl]benzoic Acid

A solution of 5.60 g (0.03 mole) of the known compound 4-amino-2,6-di-t-butylphenol in 100 ml of diethyl ether was added dropwise over a period of twenty minutes to a solution of 4.44 g (0.03 mole) of phthalic anhydride in 200 ml of a 1:2 mixture of diethyl ether:toluene. The reaction mixture was stirred at room temperature for about sixteen hours. The resulting precipitate was collected, rinsed with a mixture of diethyl ether and hexane, and dried to give 6.8 g of a white solid. This material was recrystallized from a mixture of ethyl acetate and hexane to give 5.9 g of white solid 2-[N-(3,5-di-t-butyl-4-hydroxyphenyl)carbamoyl]benzoic acid, m.p. 191°–192° C. Analysis: Calculated for $C_{22}H_{27}NO_4$: %C, 71.5; %H, 7.4, %N, 3.8; Found: %C, 71.8; %H, 7.3; %N, 3.7.

EXAMPLE 9

Preparation of 2-[N-(3,5-Di-t-butyl-4-hydroxyphenyl)carbamoyl]-cis-cyclohexanecarboxylic Acid A solution containing 5.68 g (0.03 mole) of 4-amino-2,6-di-t-butylphenol in 200 ml of diethyl ether was added dropwise to a solution of 4.62 g (0.03 mole) of cis-1,2-cyclohexanedicarboxylic anhydride in 200 ml of diethyl ether. The reaction mixture was stirred at room temperature for about sixteen hours. The resulting precipitate was collected, rinsed with a mixture of diethyl ether and hexane, and dried to give 8.1 g of a solid. This material was recrystallized from a mixture of ethyl acetate and hexane to give 7.3 g of white solid 2-[N-(3,5-di-t-butyl-4-hydroxyphenyl)carbamoyl]-cis-cyclohexanecarboxylic acid, m.p. 181°–184° C. Analysis: Calculated for $C_{22}H_{33}NO_4$: %C, 70.4, %H, 8.9; %N, 3.7; Found: %C, 70.1; %H, 8.7; %N, 3.6.

EXAMPLE 10

Preparation of 2-[N-(3,5-Di-t-butyl-4-hydroxyphenyl)carbamoyl]-trans-cyclohexanecarboxylic Acid A solution containing 4.00 g (0.022 mole) of 4-amino-2,6-di-t-butylphenol in 50 ml of 1,2-dimethoxyethane was added dropwise over a period of ten minutes to a solution of 3.35 g (0.022 mole) of trans-1,2-cyclohexanedicarboxylic anhydride in 50 ml of 1,2-dimethoxyethane. The reaction mixture was stirred at room temperature for about seventy-two hours. The solvent was removed under vacuum and the residual solid was triturated with a mixture of diethyl ether and hexane. The resulting solid was recrystallized from a mixture of ethyl acetate and hexane to give 4.4 g of white solid 2-[N-(3,5-di-t-butyl-4-hydroxyphenyl) carbamoyl]-trans-cyclohexanecarboxylic acid, m.p. 247°–252° C. Analysis: Calculated for $C_{22}H_{33}NO_4$: %C, 70.4; %H, 8.9; %N, 3.7; Found: %C, 70.4; %H, 8.9; %N, 3.6.

EXAMPLE 11

Preparation of 3-Carboxy-N(3′,5′-di-t-butyl-4′-hydroxyphenyl)benzamide

To a suspension of 5.3 g (0.029 mole) of m-(chloroformyl)benzoic acid in a mixture of 5.8 g (0.058 mole) of triethyl amine and 100 ml of methylene chloride was added 6.4 g (0.029 mole) of 4-amino-2,6-di-t-butylphenol. The resulting solution was stirred at room temperature for about sixteen hours. The solvents were removed under vacuum and the residual solid was taken up in chloroform and washed with 3N hydrochloric acid. The chloroform solution was dried with magnesium sulfate and then evaporated to give 8 g of a solid. This material was slurried in 80 ml of 20% chloroform in hexane, collected, rinsed with chilled hexane and dried to give 5.9 g of a solid. This solid was slurried in 100 ml of warm 1:1 ethyl acetate:hexane, cooled, collected, rinsed with chilled hexane and dried to give 3.2g of pale pink solid. This pale pink solid was stirred in 320 ml refluxing chloroform. The hot chloroform was filtered to remove insoluble material. The filtrate was diluted with 500 ml of hexane and the resulting precipitate was collected and dried to give 0.97 g of a very pale pink solid. This solid was then slurried in 25% acetone in hexane, collected and dried to give 0.67 g of white solid 3-carboxy-N-(3′,5′di-t-butyl-4′-hydroxyphenyl)-benzamide, m.p. 253°–257° C. Analysis: Calculated for $C_{22}H_{27}NO_4$: %C, 71.5; %H, 7.4; %N, 3.8; Found: %C, 71.9; %H, 7.4; %N, 3.6.

EXAMPLE 12

Preparation of 3-Cyano-N-(3′,5′-Di-t-butyl-4′-hydroxyphenyl)benzamide

To a solution containing 3.4 g (0.015 mole) of 4-amino-2,6-di-t-butylphenol and 2.3 g (0.015 mole) of 3-cyanobenzoic acid in 50 ml of tetrahydrofuran was added a solution containing 3.2 g (0.015 mole) of N,N′-dicyclohexylcarbodiimide in 10 ml of tetrahydrofuran. A precipitate formed immediately. The reaction mixture was allowed to stir at room temperature for about sixteen hours. The reaction mixture was filtered and the filtrate was concentrated under vacuum to give 5.7 g of a black solid. This material was triturated with 250 ml of 20% chloroform in hexane to give a tan solid. The tan solid was collected and then heated at reflux for about one hour in 100 ml of 20% chloroform in hexane. This mixture was filtered hot to provide 3.0 g of a rose solid. The rose solid was heated with 85 ml of 9:8 ethyl acetate:hexane and then filtered while still hot. The filtrate was cooled and the resulting precipitate was collected to provide 0.90g of solid 3-cyano-N-(3′,5′-di-t-butyl-4′-hydroxyphenyl) benzamide, m.p. 219°–222° C. Analysis: Calculated for $C_{22}H_{26}N_2O_2$: %C, 75.4; %H, 7.5; %N, 8.0; Found: %C, 75.4; %H, 7.5; %N, 8.0.

EXAMPLE 13

Preparation of N-(3′,5′-Di-t-butyl-4′-hydroxyphenyl)-3-(5′-tetrazolyl)-benzamide A mixture containing 2.9 g (8.28 mmole) of 3-cyano-N-(3′,5′-di-t-butyl-4′-hydroxyphenyl)benzamide, 1.6g (24.8 mmole) of sodium azide, 1.3 g (24.8 mmole) of ammonium chloride, 0.35 g (8.28 mmole) of lithium chloride and 20 ml of dimethylformamide was heated under a nitrogen atmosphere at 90° C. for about ninety-six hours. The reaction mixture was allowed to cool to room temperature and then filtered. The filtrate was added to a mixture of 50 ml 3N hydrochloric acid and ice to provide a gummy red solid. The solvents were decanted off and the solid was triturated with chloroform to provide 2.8 g of a pale pink solid. This material was stirred with 50 ml of 5% hexane in chloroform and then filtered to provide 2.2 g of a white solid m.p. 215°–217° C. 1.7 g of this material was recrystallized from a mixture of ethanol and water to provide 1.2 g of white solid N-(3′-5′-di-t-butyl-4′-hydroxyphenyl) -3-(5′-tetrazolyl)benzamide. m.p. 238°–242° C. Analysis: Calculated for: $C_{22}H_{27}H_5O_2$: %C, 67.15; %H, 6.9; %N, 17.8; Found: %C, 66.7; %H, 6.9; %N, 17.8.

EXAMPLE 14

Preparation of N-(3′,5′-Di-t-butyl-4′-hydroxyphenyl)-4-(5′-tetrazolyl)-benzamide Part A Using the method of Example 12, 3.4 g of 4-amino-2,6-di-t-butylphenol was reacted with 2.3 g of 4-cyanobenzoic acid to provide 2.7 g of 4-cyano-N-(3′,5′-di-t-butyl-4′-hydroxyphenyl)benzamide.

Part B

Using the method of Example 13 the nitrile prepared in Part A was converted to the tetrazole to provide 1.2 g of pale yellow N-(3′,5′di-t-butyl-4′-hydroxyphenyl)-4-(5′-tetrazolyl)benzamide m.p. 252°–254° C. Analysis: Calculated for $C_{22}H_{27}N_5O_2$: %C, 67.15; %H, 6.9; %N, 17.8; Found: %C, 67.0; %H, 7.0; %N, 17.9.

EXAMPLES 15–20

Table I illustrates compounds of Formula VII which could be prepared via reaction Scheme A from 3,5-di-t-butyl-4-hydroxybenzoyl chloride and the indicated compounds of Formula VI using the general method of Examples 1–6.

TABLE I

| Ex. No. | Compound of Formula VI | Product of Formula VII |
|---|---|---|
| 15 | 4-amino-3-methylbenzoic acid (NH₂–C₆H₃(CH₃)–COOH) | 3,5-di-t-butyl-4-hydroxy-N-(2-methyl-4-carboxyphenyl)benzamide |
| 16 | 4-aminocinnamic acid (NH₂–C₆H₄–CH=CHCO₂H) | 3,5-di-t-butyl-4-hydroxy-N-(4-(2-carboxyvinyl)phenyl)benzamide |
| 17 | (4-aminophenylthio)acetic acid (NH₂–C₆H₄–SCH₂CO₂H) | 3,5-di-t-butyl-4-hydroxy-N-(4-(carboxymethylthio)phenyl)benzamide |
| 18 | (4-aminophenoxy)acetic acid (NH₂–C₆H₄–OCH₂COOH) | 3,5-di-t-butyl-4-hydroxy-N-(4-(carboxymethoxy)phenyl)benzamide |
| 19 | N-methylanthranilic acid (2-(CH₃NH)–C₆H₄–COOH) | 3,5-di-t-butyl-4-hydroxy-N-methyl-N-(2-carboxyphenyl)benzamide |
| 20 | 2-amino-4-(trifluoromethyl)benzoic acid (NH₂–C₆H₃(CF₃)–COOH) | 3,5-di-t-butyl-4-hydroxy-N-(2-carboxy-4-trifluoromethylphenyl)benzamide |

EXAMPLES 21-27

Table II illustrates compounds of Formula X which could be prepared via Reaction Scheme B from 3,5-di-t-butyl-4-hydroxybenxoyl chloride and the indicated compounds of Formula VIII via the indicated intermediates of Formula IX using the general method of Example 7.

TABLE II

| Ex. No. | Compound of Formula VIII | Intermediate of Formula IX | Product of Formula X |
|---|---|---|---|
| 21 | NH₂–C₆H₄–CN | 3,5-di-t-butyl-4-hydroxy-N-(4-cyanophenyl)benzamide | 3,5-di-t-butyl-4-hydroxy-N-(4-(tetrazol-5-yl)phenyl)benzamide |

TABLE II-continued
| Ex. No. | Compound of Formula VIII | Intermediate of Formula IX | Product of Formula X |
|---|---|---|---|
| 22 | 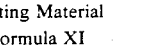 | | |
| 23 | | | |
| 24 | | | |
| 25 | | | |
| 26 | | | |
| 27 | | | |
EXAMPLES 28–32
Table III illustrates compounds of Formula X which could be prepared via Reaction Scheme B from 3,5-di-t-butyl-4-hydroxybenxoyl chloride and the indicated compounds of Formula XI.
TABLE III
| Ex. No. | Starting Material of Formula XI | Product of Formula X |
|---|---|---|
| 28 | 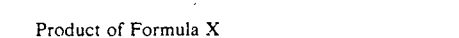 | |

TABLE III-continued

| Ex. No. | Starting Material of Formula XI | Product of Formula X |
|---|---|---|
| 29 | | |
| 30 | | |
| 31 | | |
| 32 | | |

The claimed invention is:

1. A compound of the formula

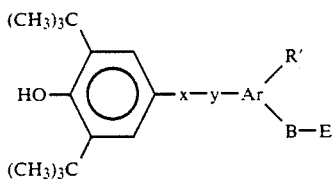

wherein x is carbonyl or N-R, and y is carbonyl or N-R; with the proviso that when x is carbonyl, y is N-R, and when x is N-R, y is carbonyl; further provided that:

1)
   when x is N-R,
   R is hydrogen,
   R' is hydrogen,
   B is a carbon-carbon bond,
   Ar is phenyl or cyclohexyl, and
   E is tetrazolyl or carboxyl,
   with the proviso that when Ar is cyclohexyl, E is carboxyl and is alpha to the carbonyl-cyclohexyl bond; and 2)
   when x is carbonyl,
   R is hydrogen or lower alkyl,
   R' is hydrogen, halogen, trifluoromethyl, lower alkyl or lower alkoxy,
   Ar is phenyl,
   E is carboxyl, tetrazolyl, or N-methyltetrazolyl, and
   B is as follows:
   when E is carboxyl, B is a carbon-carbon bond; an alkylene group containing one to about seven carbon atoms; or an alkylene group containing one to about seven carbon atoms and being either (a) interrupted by an ether linkage, a thioether linkage or a carbon-carbon double bond, or (b) attached to the phenyl ring by an oxygen atom or an unoxidized sulfur atom; or
   when E is tetrazolyl or N-methyltetrazolyl, B is a carbon-carbon bond; an alkylene group containing one to about four carbon atoms; an alkylene group containing one to about four carbon atoms and being either (a) interrupted by an ether linkage, a thioether linkage or a carbon-carbon double bond, or (b) attached to the phenyl ring by an oxygen atom or an unoxidized sulfur atom; an unoxidized sulfur atom; or carboxamido;

or a derivative of said compound wherein E is carboxyl, selected from the group consisting of a lower alkyl ester, a (lower)alkylamino(lower)alkyl ester, an ester of glycolamide, a pharmaceutically acceptable (lower)alkylamino(lower)alkyl ester acid-addition salt and a pharmaceutically acceptable carboxylate salt;
or a derivative of said compound wherein E is tetrazolyl, selected from a pharmaceutically acceptable alkali metal or alkaline earth salt of the tetrazolyl moiety.

2. A compound according to claim 1 wherein X is carbonyl.

3. A compound according to claim 1, wherein X is N-R.

4. A compound according to claim 3, wherein Ar is cyclohexyl.

5. A compound according to claim 3, wherein Ar is phenyl.

6. A compound according to claim 3, wherein E is carboxyl.

7. A compound according to claim 3, wherein E is tetrazolyl.

8. A compound according to claim 2, wherein E is carboxyl.

9. A compound according to claim 2, wherein E is tetrazolyl.

10. N-(4-carboxyphenyl)-3,5-di-t-butyl-4-hydroxybenzamide according to claim 2.

11. N-(2-carboxyphenyl)-3,5-di-t-butyl-4-hydroxybenzamide according to claim 2.

12. 5-[3-(3,5-di-t-butyl-4-hydroxybenzamido)phenyl]-tetrazole according to claim 2.

13. N-(3-carboxyphenyl)-3,5-di-t-butyl-4-hydroxybenzamide according to claim 2.

14. 4-(3,5-di-t-butyl-4-hydroxybenzamido)phenylacetic acid according to claim 2.

15. N-(3-carboxy-4-chlorophenyl)-3,5-di-t-butyl-4-hydroxybenzamide according to claim 2.

16. N-(5-carboxy-2-methoxyphenyl)-3,5-di-t-butyl-4-hydroxybenzamide according to claim 2.

17. 5-[3-(3,5-di-t-butyl-4-hydroxybenzamido)phenyl]-tetrazole hydrate according to claim 2.

18. 2-[N-(3,5-dit-butyl-4-hydroxyphenyl)carbamoyl]-benzoic acid according to claim 3.

19. 2-[N-(3,5-di-t-butyl-4-hydroxyphenyl)carbamoyl)]-cis-cylclohexane carboxylic acid according to claim 3.

20. 2-[N-(3,5-di-t-butyl-4-hydroxyphenyl)carbamoyl]-trans-cyclohexane carboxylic acid according to claim 3.

21. 3-carboxy-N-(3',5'-di-t-butyl-4'-hydroxyphenyl)-benzamide according to claim 3.

22. N-(3',5'-di-t-butyl-4'-hydroxyphenyl)-3-(5'-tetrazolyl) benzamide according to claim 3.

23. N-(3',5'-di-t-butyl-4'-hydroxyphenyl)-4-(5'-tetrazolyl)benzamide according to claim 3.

24. An antiallergic pharmaceutical composition comprising a compound according to claim 1 and a pharmaceutically acceptable vehicle, the compound being present in an amount effective for obtaining an antiallergic response in a mammal.

25. A method for inhibiting bronchoconstriction due to an allergic response in a mammal wherein a compound according to claim 1 is administered to the mammal in an amount effective for obtaining such inhibition.

26. A method for inhibiting leukotriene biosynthesis in a mammal comprising administering to the mammal a compound according to claim 1 in an amount effective to inhibit the biosynthesis.

* * * * *